United States Patent [19]

Johnson

[11] Patent Number: 4,861,927

[45] Date of Patent: Aug. 29, 1989

[54] DEHYDROHALOGENATION OF RING-HALOGENATED α-HALOCUMENES

[75] Inventor: Mark R. Johnson, Grayslake, Ill.

[73] Assignee: The Dow Chemical Company, Midland, Mich.

[21] Appl. No.: 253,455

[22] Filed: Oct. 5, 1988

Related U.S. Application Data

[63] Continuation-in-part of Ser. No. 53,924, May 26, 1987, abandoned.

[51] Int. Cl.$^4$ .................... C07C 17/24; C07C 17/34; C07C 21/24
[52] U.S. Cl. .................................. 570/200; 570/144
[58] Field of Search ........................................ 570/200

[56] References Cited

U.S. PATENT DOCUMENTS

| | | | |
|---|---|---|---|
| 1,687,903 | 10/1928 | Smith | 585/433 |
| 2,231,026 | 2/1941 | Quattlebaum et al. | 260/669 |
| 2,295,077 | 9/1942 | Dreisbach et al. | 260/650 |
| 2,363,011 | 11/1944 | Michalek et al. | 260/650 |
| 2,432,737 | 12/1947 | Erickson et al. | 260/650 |
| 2,485,524 | 10/1949 | Basdekis | 260/650 |
| 2,486,379 | 11/1949 | Amos et al. | 260/650 |
| 2,507,506 | 5/1950 | Dreisbach et al. | 260/462 |
| 2,519,125 | 8/1950 | Erickson | 260/650 |
| 2,564,507 | 8/1951 | Schaeffer | 260/650 |
| 2,609,403 | 9/1952 | Salt et al. | 260/650 |
| 2,618,628 | 11/1952 | Haus | 260/91.5 |
| 3,067,182 | 12/1962 | Jones | 260/87.5 |
| 3,274,077 | 9/1966 | Hoffenberg et al. | 203/8 |
| 3,927,117 | 12/1975 | Bianchi | 260/613 |
| 3,966,831 | 6/1976 | Levy et al. | 570/200 |
| 4,045,501 | 8/1977 | Bianchi | 260/651 |
| 4,087,473 | 5/1978 | Markley | 260/651 |
| 4,104,315 | 8/1978 | Dewald et al. | 260/650 |
| 4,188,346 | 2/1980 | Markley | 260/651 |
| 4,205,015 | 5/1980 | Wang et al. | 260/651 |
| 4,211,548 | 7/1980 | Franz et al. | 558/169 |
| 4,230,642 | 10/1980 | Nishiyama et al. | 570/193 |
| 4,292,453 | 9/1981 | Daren et al. | 570/193 |
| 4,329,524 | 5/1982 | Dewald | 570/190 |
| 4,594,467 | 6/1986 | Henneke et al. | 570/193 |
| 4,633,026 | 12/1986 | Kolich | 570/200 |
| 4,686,311 | 8/1987 | Jackisch | 570/200 |
| 4,748,286 | 5/1988 | Daren et al. | 570/200 |
| 4,760,209 | 7/1988 | Blank et al. | 570/200 |

FOREIGN PATENT DOCUMENTS

| | | | |
|---|---|---|---|
| 792860 | 4/1958 | United Kingdom . | |
| 986634 | 3/1965 | United Kingdom | 570/200 |

OTHER PUBLICATIONS

GB 1231179, Derwent #30987s, LaPorte Chem., May 12, 1971.
Dehydrohalogenation of Halogen-Containing Polymers, 105:1156026.

*Primary Examiner*—J. E. Evans
*Attorney, Agent, or Firm*—Craig E. Mixan; Ronald G. Brookens

[57] ABSTRACT

A process for preparing ring-halogenated α-methylstyrenes from the corresponding α-halocumens is disclosed. The dehydrohalogenation is accomplished using only water and optionally an organic solvent. The process eliminates the need for added base and a phase-transfer catalyst.

8 Claims, No Drawings

DEHYDROHALOGENATION OF RING-HALOGENATED α-HALOCUMENES

This application is a continuation-in-part of applicant's copending application Ser. No. 053,924, filed May 26, 1987, now abandoned.

FIELD OF THE INVENTION

The present invention relates to a process for preparing ring-substituted α-methylstyrenes. More particularly the present invention relates to the preparation of ring halogenated α-methylstyrenes by the dehydrohalogenation of the corresponding ring-halogenated α-halocumenes.

BACKGROUND OF THE INVENTION

Ring-halogenated α-methylstyrenes are intermediates for the preparation of plant-protection agents (see, for example, U.S. Pat. No. 4,211,548). U.S. Pat. No. 4,594,467 describes a process in which 3,5-dichloro-α-methylstyrene is prepared by the dehydrobromination of α-bromo-3,5-dichlorocumene with an alkali metal hydroxide solution in the presence of a phase-transfer catalyst above 70degrees Centigrade (°C.). While this process enjoys excellent yields, it has the disadvantage of requiring the use of expensive and often toxic phase-transfer catalysts that must be removed after completion of the reaction. The separation of catalyst from the reaction mixture often requires multiple unit operations. After separation, the phase-transfer catalyst requires recycle or disposal. It would be clearly beneficial to have an efficient process that eliminates the need of the phase-transfer catalyst.

Furthermore, the process described hereinabove utilizes a caustic or basic medium such as, for example, sodium hydroxide. Such caustic solutions are incompatible with glass-lined vessels. Again, it is highly desirable to have a process that does not require the addition of a base to accomplish the desired elimination.

SUMMARY OF THE INVENTION

The present invention is directed to a process for preparing a ring-halogenated c-methylstyrene compound of the Formula (I)

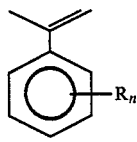

(I)

wherein

R represents halogen and n represents 1 or 2 which comprises contacting a ring-halogenated α-halocumene compound of the Formula (II)

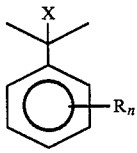

(II)

wherein

X is chloro or bromo and R and n are as previously defined with water at ambient pressure and at a temperature from about 70° to about 130° C. in the absence of an added base and in the absence of a phase-transfer catalyst.

As used herein, the term halogen refers to fluorine, chlorine, bromine and iodine.

With respect to the ring-halogenated α-methylstyrene of Formula (I), R is preferably chloro, and n is preferably 2. It is also preferred that R is substituted in the 3- and/or 5-positions of the phenyl ring. Most preferably, R is chloro, n is 2, and R is substituted at the 3- and 5-positions on the ring, i.e., the compound known as 3,5-dichloro-α-methylstyrene.

With respect to the ring-halogenated α-halocumene of Formula (II), X is preferably bromo. It is also preferred that R is chloro, and n is 2. It is further preferred that R is substituted in the 3-and/or 5-positions of the phenyl ring. Most preferably, X is bromo, R is chloro, n is 2, and R is substituted at the 3- and 5-positions on the ring, i.e., the compound known as α-bromo-3,5-dichlorocumene.

The present invention has the advantage of preparing ring-halogenated α-methylstyrenes without the need for a phase-transfer catalyst and without the need for an added base.

DETAILED DESCRIPTION OF THE INVENTION

The heating of the α-halocumene starting material of Formula (II) with water is carried out at temperatures ranging from about 70° to about 130° C., preferably from about 95° to about 115° C.

Optionally, the reaction mixture may also contain a liquid inert organic solvent in an amount effective to at least dissolve the α-halocumene compound of Formula (II) so as to improve the handling of this starting material and the recovery of the product. Representative inert organic solvents suitable for dissolving the α-halocumene compound include but are not limited to halogenated aromatics and aliphatic hydrocarbons such as chlorobenzene, chloroform, carbon tetrachloride; or non-halogen containing aromatic or aliphatic hydrocarbons such as benzenes, xylenes, hexane, cyclohexane, pentanes, etc. Generally, the inert organic solvent can be present in an amount ranging from 0 to about 2 parts by weight inert organic solvent to about 1 part by weight α-halocumene, preferably from about 0 to about 1 part by weight inert organic solvent.

Water, at least equivalent in quality to that used for industrial purposes, can be used in the process of the present invention. The amount of water in association with the α-halocumene of Formula (III) should be an amount effective to promote dehydrohalogenation of said α-halocumene. Generally, water is present in an amount ranging from about 1 to about 4 parts by weight α-halocumene to about one part by weight water, preferably from about one part water to about 1.1 to about 1 part by weight α-halocumene.

The heating of the α-halocumene and water, and optionally, organic solvent should be maintained for a period effective to convert the α-halocumene to α-methylstyrene, preferably from about 1 to about 24 hours (hr), more preferably from about 2 to about 6 hr. The reaction mixture should be stirred during the course of the heating.

Separation to recover the desired α-methylstyrene compound of Formula (I) from the reaction mixture can be accomplished by phase separation of the aqueous and organic layers. The organic layer containing the desired α-methylstyrene compound can be treated by conventional procedures, such as stripping, distillation, or crystallization.

The following examples illustrate the present invention in a manner by which it can be practiced but, as such, should not be construed as limitations upon the overall scope of the same.

EXAMPLE 1

A sample of 273.2 g of crude α-bromo-3,5-dichlorocumene (BrDCC-62.4 percent purity) with the balance monochlorobenzene (MCB) is treated with 100 milliliters (ml) water, and the mixture is stirred and heated at 100°–105° C. for 3.5 hr. Phase inversion of the water and the organic layer occurs after about 1 hr. After 3.5 hr an additional 50 ml water is added, and the mixture is heated an additional 2 hr. The mixture is allowed to cool, the phases are separated by decantation, the product phase is washed with an additional 25 ml water, and the aqueous phase is extracted with an additional 10 ml MCB. The crude product weighs 225.4 g and contains 50.8 percent 3,5-dichloro- α-methylstyrene (DCAMS-96 percent yield). Distillation is done through a short Vigreaux column. MCB is removed at 15–20 millimeters (Mm) mercury (Hg) at an overhead temperature of 35° C. The fraction containing 3,5-dichloro- α-methylstyrene is taken at an overhead temperature of 108°–110° C. The product cut contains a 94 percent yield of 3,5-dichloro- α-methylstyrene.

EXAMPLE 2

A sample of 124.3 g of crude solvent-free α-bromo-3,5-dichlorocumene (BrDCC-91 percent purity) and 93 ml of water are stirred and heated at 100°–110° C. for 3 hr. The mixture is allowed to cool, the phases are separated by decantation, and the product phase washed with 10 ml water. The product is distilled through a short Vigreaux column under vacuum with an overhead temperature of 157°–160° C. and the pot temperature is maintained at 155°–200° C. The overheads contain a 95 percent yield of 3,5-dichloro-α-methylstyrene.

What is claimed is:

1. A process for preparing a ring-halogenated α-methylstyrene of the Formula (1)

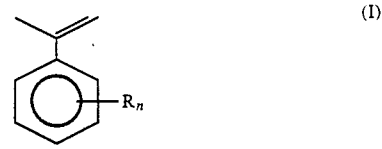

wherein
R represents halogen and n represents 1 or 2 which comprises contacting a ring-halogenated α-halocumene of the Formula (II)

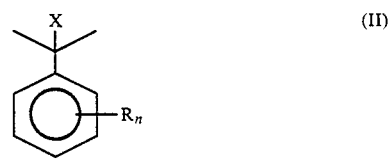

wherein
X is chloro or bromo and R and n are as previously defined
with water at ambient pressure and at a temperature from about 70° to about 130° C. in the absence of an added base and in the absence of a phase-transfer catalyst.

2. The process of claim 1 in which R is chloro.
3. The process of claim 1 in which n is 2.
4. The process of claim 1 in which R is chloro and n is 2.
5. The process of claim 1 in which X is bromo.
6. The process of claim 4 in which R is substituted in the 3- and 5-positions on the phenyl ring.
7. The process of claim 1 in which the mixture is heated to a temperature ranging between 95° and 115° C.
8. The process of claim 1 in which a hydrocarbon or halohydrocarbon solvent is employed.

* * * * *